United States Patent
Masumoto et al.

(10) Patent No.: US 9,456,788 B2
(45) Date of Patent: Oct. 4, 2016

(54) IMAGE PROCESSING DEVICE, METHOD AND NON-TRANSITORY STORAGE MEDIUM

(71) Applicant: FUJIFILM Corporation, Tokyo (JP)

(72) Inventors: Jun Masumoto, Tokyo (JP); Yuanzhong Li, Tokyo (JP); Yoshinori Itai, Tokyo (JP); Yasunori Ohta, Tokyo (JP); Yoshinao Fujimori, Tokyo (JP); Keigo Nakamura, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 68 days.

(21) Appl. No.: 14/485,446

(22) Filed: Sep. 12, 2014

(65) Prior Publication Data
US 2015/0003710 A1    Jan. 1, 2015

Related U.S. Application Data

(63) Continuation of application No. PCT/JP2012/075332, filed on Oct. 1, 2012.

(30) Foreign Application Priority Data

Mar. 26, 2012    (JP) ................................. 2012-068698

(51) Int. Cl.
*A61B 5/00* (2006.01)
*A61B 5/055* (2006.01)
*A61B 6/00* (2006.01)
(Continued)

(52) U.S. Cl.
CPC .............. *A61B 5/7232* (2013.01); *A61B 5/004* (2013.01); *A61B 5/0037* (2013.01); *A61B 5/0073* (2013.01); *A61B 5/055* (2013.01); *A61B 5/08* (2013.01); *A61B 5/7235* (2013.01); *A61B 6/486* (2013.01); *G06T 7/0028* (2013.01); *A61B 5/0035* (2013.01); *A61B 6/5247* (2013.01); *A61B 8/5261* (2013.01); *A61B 2576/02* (2013.01);
(Continued)

(58) Field of Classification Search
None
See application file for complete search history.

(56) References Cited

U.S. PATENT DOCUMENTS 6,628,434 B1    9/2003  Yasuda
6,904,163 B1 *  6/2005  Fujimura .............. G06T 7/0012
                                                     378/162

(Continued)

FOREIGN PATENT DOCUMENTS

JP    11-27680 A       1/1999
JP    2001-103222 A    4/2001
(Continued)

OTHER PUBLICATIONS

International Search Report (ISR) (PCT Form PCT/ISA/210), in PCT/JP2012/075332, dated Dec. 25, 2012.
(Continued)

*Primary Examiner* — Siamak Harandi
*Assistant Examiner* — Pinalben Patel
(74) *Attorney, Agent, or Firm* — McGinn IP Law Group, PLLC (57) ABSTRACT

At least one of the common regions in time-sequence images is specified. Then, the time-sequence images are adjusted such that the position of that common region in at least one image among the time-sequence images is adjusted to the position of that common region in a different image. Then, the new adjusted time-sequence images are subjected to video compression processing.

14 Claims, 9 Drawing Sheets

(51) Int. Cl.
  *A61B 5/08* (2006.01)
  *G06T 7/00* (2006.01)
  *A61B 8/08* (2006.01)

(52) U.S. Cl.
  CPC ............... *G06T2207/10072* (2013.01); *G06T 2207/30004* (2013.01)

(56) References Cited

U.S. PATENT DOCUMENTS

| | | | | |
|---|---|---|---|---|
| 7,620,229 | B2 * | 11/2009 | Oosawa | A61B 6/032 382/128 |
| 2003/0035584 | A1 * | 2/2003 | Nicolas | G06F 19/321 382/232 |
| 2005/0111757 | A1 * | 5/2005 | Brackett | A61B 6/463 382/294 |
| 2007/0269089 | A1 * | 11/2007 | Sakaida | G06K 9/38 382/128 |
| 2008/0039707 | A1 * | 2/2008 | Sugiyama | G06F 19/321 600/407 |
| 2008/0175453 | A1 * | 7/2008 | Hao | G01S 7/52077 382/128 |
| 2008/0219567 | A1 * | 9/2008 | Claus | H04N 19/593 382/232 |
| 2009/0005679 | A1 * | 1/2009 | Dala-Krishna | A61B 8/0883 600/437 |
| 2010/0157041 | A1 * | 6/2010 | Klaiman | G06T 7/0022 348/77 |
| 2012/0082356 | A1 * | 4/2012 | Zankowski | G06T 9/00 382/131 |
| 2012/0230563 | A1 * | 9/2012 | Vik | A61B 6/032 382/128 |
| 2014/0064554 | A1 * | 3/2014 | Coulter | G06K 9/3216 382/103 |

FOREIGN PATENT DOCUMENTS

| | | |
|---|---|---|
| JP | 2003-126046 A | 5/2003 |
| JP | 2005-245922 A | 9/2005 |
| JP | 2006-6797 A | 1/2006 |
| JP | 2009-291280 A | 12/2009 |
| JP | 4855141 B2 | 1/2012 |

OTHER PUBLICATIONS

Japanese Office Action dated Jun. 23, 2015 with a partial English translation thereof.

* cited by examiner

IMAGE PROCESSING DEVICE, METHOD AND NON-TRANSITORY STORAGE MEDIUM

CROSS-REFERENCE TO RELATED APPLICATIONS AND PRIORITY CLAIM

This application is a Continuation of International Application No. PCT/JP2012/075332 filed on Oct. 1, 2012, which was published under PCT Article 21(2) in Japanese, which is based upon and claims the benefit of priority from Japanese Patent Application No. 2012-068698 filed on Mar. 26, 2012, the contents all of which are incorporated herein by reference.

TECHNICAL FIELD

The present invention relates to an image processing apparatus, an image processing method, and a non-transitory storage medium.

BACKGROUND ART

Recently, in the medical field, due to the rapid development of high-performance image capturing apparatus (or modality) and dose reduction technology, the number of medical images that can be acquired per each examination process has been increasing. However, since such an increased number of acquired medical images results in a vast amount of data that must be handled by an overall medical diagnostic system, problems arise such as a sharp increase in the cost of data storage and transmission. It is effective to reduce the amount of data to be handled by performing an image compression process on the medical images before the medical images are transmitted or saved (see Japanese Laid-Open Patent Publication No. 2003-126046). Various technologies for increasing the efficiency with which images are compressed have been proposed in the art.

According to Japanese Laid-Open Patent Publication No. 2009-291280, there have been proposed a system for and a method of sorting a sequence of cross-sectional images along a direction in which pixels of the images change. Then, the sorted images are regarded as a moving image, and an image compression process is performed thereon.

According to Japanese Laid-Open Patent Publication No. 2005-245922, a method and an apparatus have been proposed in which blocks of image data concerning pixels that share positions are encoded, and thereafter, the encoded blocks are sorted into groups in order to compress the image data.

SUMMARY OF INVENTION

The methods, etc., disclosed in Japanese Laid-Open Patent Publication No. 2009-291280 and Japanese Laid-Open Patent Publication No. 2005-245922 attempt to increase compression efficiency by focusing on a change in an image between adjacent frames, and sorting (or grouping) cross-sectional images in order to reduce the amount of change. However, in case the structure of a subject that has been imaged is known, or in case a time-dependent change in the structure is comparatively small, there is sufficient room for further increasing the efficiency with which a time series of images representing the structure can be compressed.

The present invention has been made in order to solve the aforementioned problems. An object of the present invention is to provide an image processing apparatus, an image processing method, and a storage medium, which are capable of further increasing the efficiency with which a time series of images can be compressed.

According to the present invention, there is provided an image processing apparatus comprising a time-series image acquirer for acquiring time-series images made up of a plurality of raw images generated in a time series, a common region designator for designating at least one common region that is commonly included in the time-series images acquired by the time-series image acquirer, a positioning processor for adjusting the time-series images by bringing a common region that is represented by at least one raw image of the time-series images into positional alignment with a common region that is represented by another raw image, and an image compression processor for performing a moving-image compression process on new time-series images adjusted by the positioning processor.

Since the image processing apparatus includes the positioning processor, which brings a common region that is represented by at least one raw image of the time-series images into positional alignment with a common region that is represented by another raw image, at least in the common region, it is possible to generate time-series images having a small interframe image change. Further, in a case where the adjusted new time-series images are compressed, the time-series images can be compressed with increased efficiency.

Preferably, the time-series image acquirer acquires, as the time-series images, a time series of cross-sectional image groups, which are generated by capturing slice images along an axial direction, and the positioning processor adjusts the time-series images by positioning the common region along the axial direction.

Preferably, the positioning processor adjusts the time-series images by using the position of the common region, which is represented by one raw image of the time-series images as a reference, and bringing a common region that is represented by remaining raw images into positional alignment with the reference.

Preferably, the positioning processor adjusts the time-series images by positioning the common region along a cross-sectional direction normal to the axial direction.

Preferably, the time-series image acquirer acquires, as the time-series images, a cross-sectional image group generated by capturing slice images along an axial direction, and the positioning processor adjusts the time-series images by positioning the common region along a cross-sectional direction normal to the axial direction.

Preferably, the positioning processor adjusts the time-series images by bringing the common region, which is represented by each of the raw images, into positional alignment with the common region that is represented by an adjacent raw image in a time series.

Preferably, the common region designator designates, as the common region, at least one of a lung, a liver, a heart, a spleen, a kidney, a head, and a body.

According to the present invention, there also is provided an image processing method comprising an acquiring step of acquiring time-series images made up of a plurality of raw images generated in a time series, a designating step of designating at least one common region that is commonly included in the acquired time-series images, a positioning step of adjusting the time-series images by bringing a common region that is represented by at least one raw image of the time-series images into positional alignment with a common region that is represented by another raw image, and a compressing step of performing a moving-image compression process on adjusted new time-series images.

Preferably, the positioning step further acquires positioning data for positioning the common regions, the image processing method further comprising a storing step of storing compressed data generated by the compressing step, the compressed data being associated with the positioning data.

According to the present invention, there further is provided a non-transitory computer-readable recording medium storing a program therein, the program causing a computer to carry out the steps of acquiring time-series images made up of a plurality of raw images generated in a time series, designating at least one common region that is commonly included in the acquired time-series images, adjusting the time-series images by bringing a common region that is represented by at least one raw image of the time-series images into positional alignment with a common region that is represented by another raw image, and performing a moving-image compression process on adjusted new time-series images.

With the image processing apparatus, the image processing method, and the recording medium according to the present invention, inasmuch as a common region that is represented by at least one raw image of the time-series images is brought into positional alignment with a common region that is represented by another raw image, at least in the common regions, it is possible to generate time-series images having a small interframe image change. Further, in a case where the adjusted new time-series images are compressed, the time-series images can be compressed with increased efficiency.

DESCRIPTION OF EMBODIMENTS

Image processing methods according to preferred embodiments of the present invention, in relation to an image processing apparatus and a recording medium (program) for carrying out the image processing methods, will be described below with reference to the accompanying drawings.

[System Arrangement Common to the Embodiments]

Figure 1:
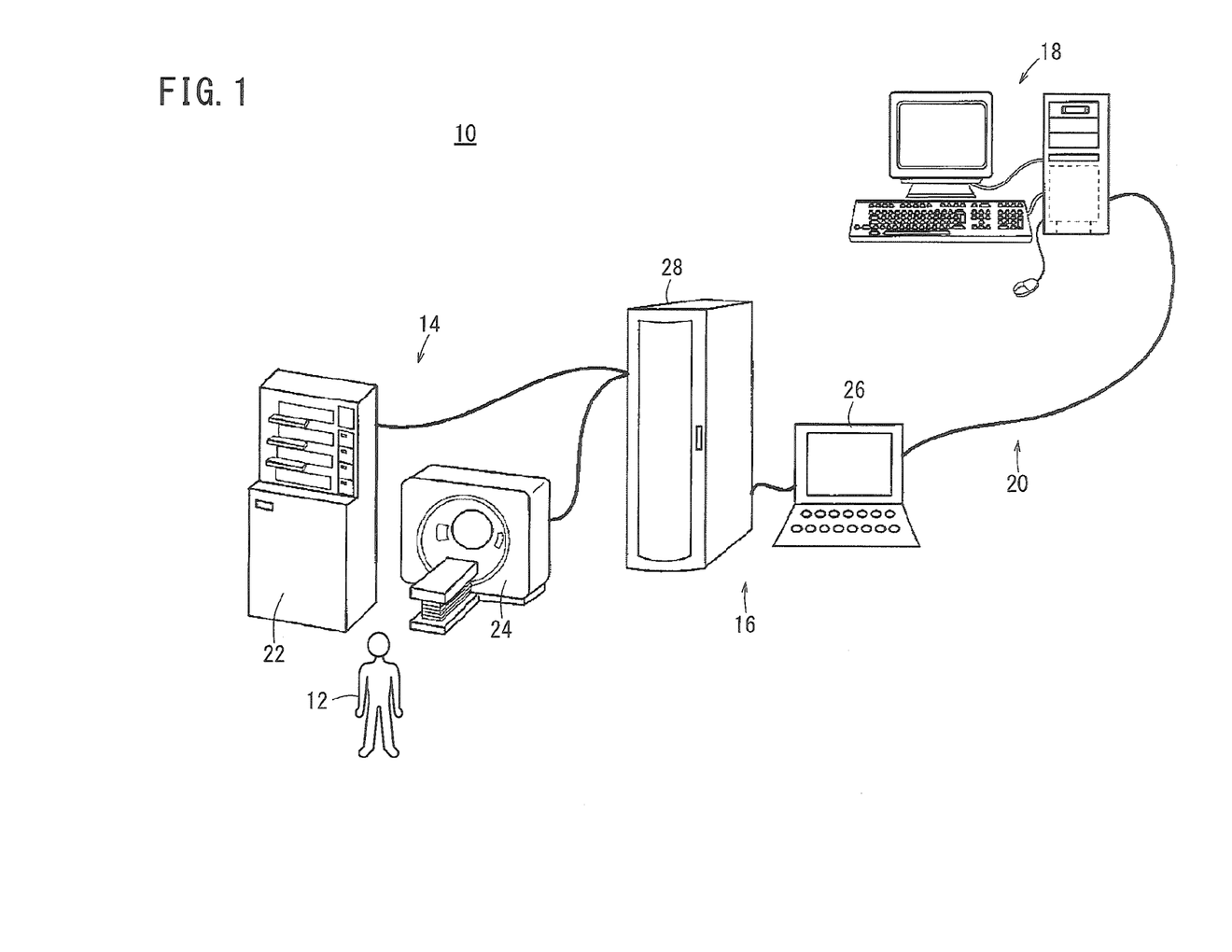
FIG. 1 is a schematic view of a medical diagnostic system incorporating an image processing apparatus according to first and second embodiments of the present invention.

FIG. 1 is a schematic view of a medical diagnostic system 10, which incorporates therein an image processing apparatus 26 according to first and second embodiments of the present invention.

The medical diagnostic system 10 basically includes a modality 14 for generating a medical image of a subject 12, an image server 16 for saving and managing medical images, and an image diagnosing apparatus 18 for displaying medical images for diagnosis or the like. The modality 14, the image server 16, and the image diagnosing apparatus 18 are connected to each other over a network 20.

The modality 14 captures an image of the subject 12 to thereby generate a medical image for diagnosis. The modality 14 outputs the generated medical image and ancillary information (image capturing conditions and information concerning the subject 12, etc.) to the image server 16. In the illustrated example, the modality 14 comprises a CR (Computed Radiography) apparatus 22 and an X-ray CT (Computed Tomography) apparatus 24. However, the modality 14 is not limited to such an apparatus configuration, and may consist of a combination of other types of image generating apparatus including a DR (Digital Radiography) apparatus, an MRI (Magnetic Resonance Imaging) apparatus, an ultrasonic (US) diagnosing apparatus, and a PET (Positron Emission Tomography) apparatus, etc., for example.

The image server 16 includes an image processing apparatus 26, which is constituted by a computer for performing a desired image processing process on the medical image supplied from the modality 14, and a storage device 28 for saving and managing the medical image that is processed by the image processing apparatus 26.

Figure 2:
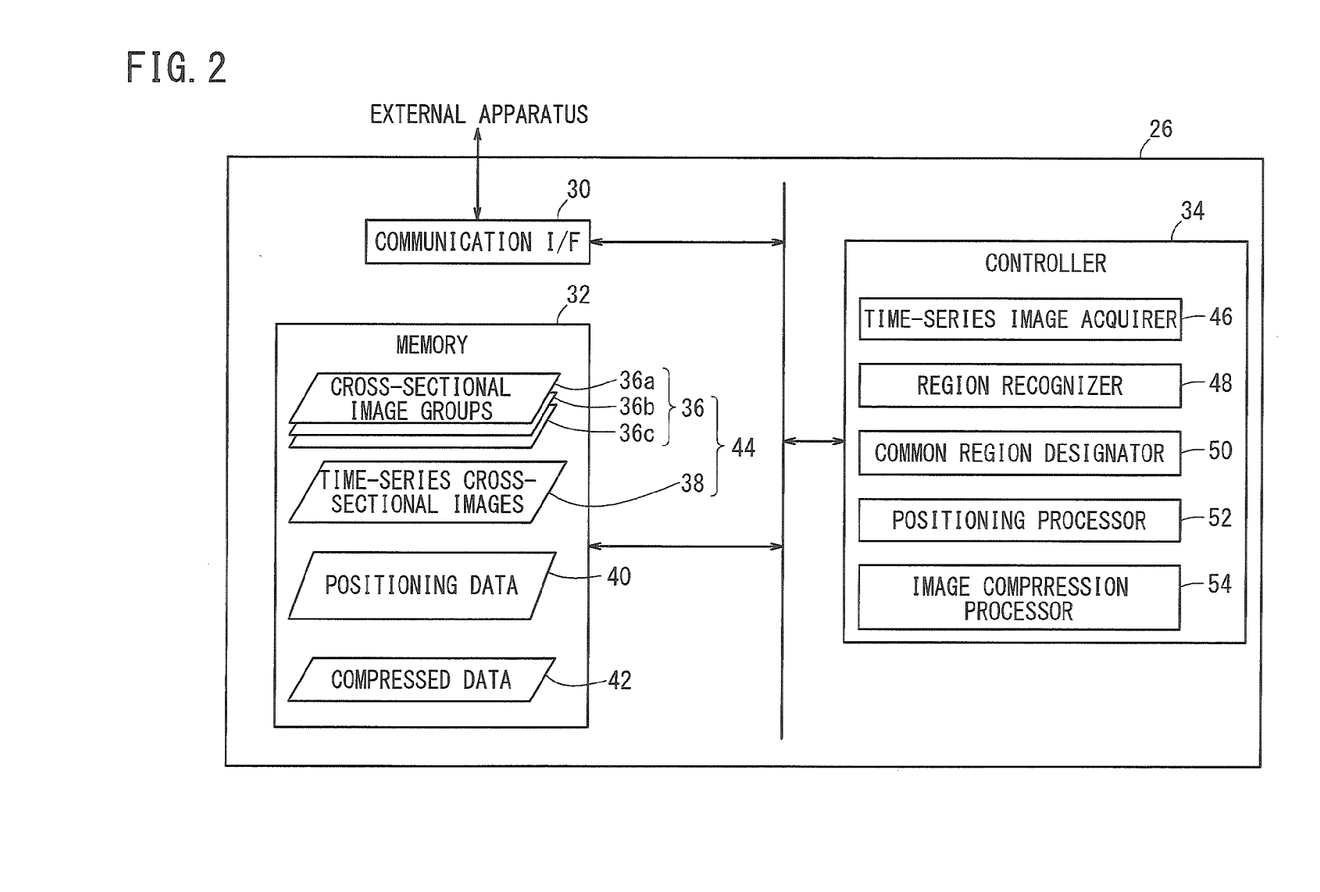
FIG. 2 is an electric block diagram of the image processing apparatus shown in FIG. 1.

FIG. 2 is an electric block diagram of the image processing apparatus 26 shown in FIG. 1. The image processing apparatus 26 includes a communication I/F 30, a memory 32 (storage medium), and a controller 34.

The communication I/F 30 comprises an interface for sending electric signals to and receiving electric signals from an external apparatus. The image processing apparatus 26 acquires a medical image, which is saved and managed by the storage device 28 (see FIG. 1) through the communication I/F 30. The medical image may be a two-dimensional image or a three-dimensional image. More specifically, the medical image may comprise a radiographic image (a so-called non-contrast radiographic image), a CT image, an MRI image, a PET image, or the like.

The memory 32 stores programs and data required for the controller 34 to control various components. The memory 32 may comprise a computer-readable non-transitory storage medium, such as a nonvolatile memory, a hard disk, or the like. As shown in FIG. 2, the memory 32 is illustrated as being capable of storing a time-series cross-sectional image group 36 including three cross-sectional image groups 36a, 36b, and 36c, time-series cross-sectional images 38, positioning data 40, and compressed data 42. Plural raw images (the time-series cross-sectional image group 36, the time-series cross-sectional images 38), which are captured time series of images of the same subject 12, are referred to collectively as "time-series images 44".

The controller 34 comprises an information processor such as a CPU (Central Processing Unit) or the like. In a case where the controller 34 reads and executes programs that are stored in the memory 32, the controller 34 functions as a time-series image acquirer 46 that acquires time-series images 44, a region recognizer 48 that recognizes a region (tissue) of the subject 12 that is included in the time-series images 44, a common region designator 50 that designates at least one region (hereinafter referred to as a "common region") that is commonly included in the time-series images 44, a positioning processor 52 that aligns the position of a common region, which is represented by at least one raw image of the time-series images 44, with the position of another common region, which is represented by another raw image, and an image compression processor 54 that performs a moving-image compression process on time-series images (new time-series images) that have been positioned by the positioning processor 52.

The image processing apparatus 26 according to the first and second embodiments are configured as described above. Operations of the image processing apparatus 26 will be described in detail below primarily with reference to flowcharts shown in FIGS. 3 and 7.

[First Embodiment]

A first embodiment for performing an image compression process on a time series of cross-sectional image groups, which are captured and generated at different times, will be described below with reference to FIGS. 3 through 6C.

Figure 3:
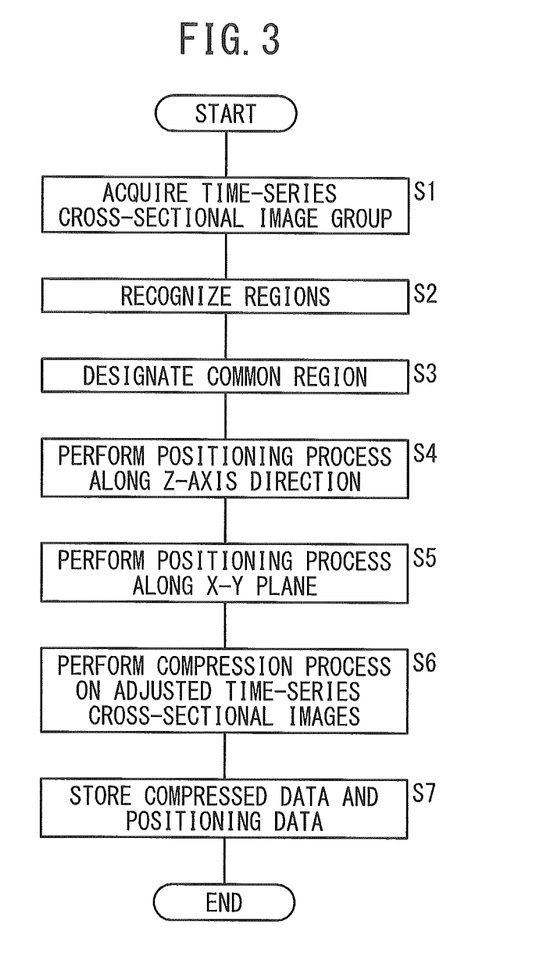
FIG. 3 is a first flowchart of an operation sequence of the image processing apparatus shown in FIGS. 1 and 2.

In step S1 of FIG. 3, the image processing apparatus 26 acquires a time-series cross-sectional image group 36, which represents a time series of cross-sectional image groups, through the communication I/F 30. More specifically, the image processing apparatus 26 acquires a time-series cross-sectional image group 36, which is obtained by capturing images of the same subject 12. The captured images are saved as medical images in the storage device 28.

Figure 4:
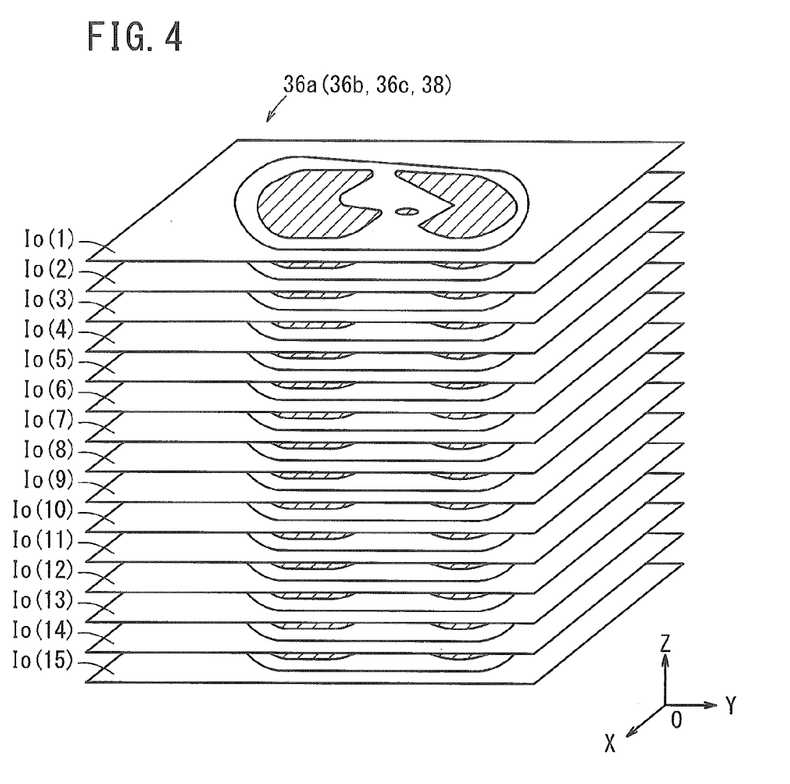
FIG. 4 is a schematic view showing by way of example a cross-sectional image group representing a chest of a subject.

FIG. 4 is a schematic view showing by way of example a cross-sectional image group 36a that represents a chest of the subject 12. The cross-sectional image group 36a is made up of raw images Io(1) through Io(N) (where, for example, N=15 as shown in FIG. 4), in which the raw images make up a plurality of cross-sectional images parallel to an X-Y plane (each of an X-axis and a Y-axis). The cross-sectional images are arranged at equal intervals along a Z-axis (predetermined axis). According to the first embodiment, for constituting the time-series cross-sectional image group 36, it is assumed that the image processing apparatus 26 acquires a cross-sectional image group 36a in a first image capturing process, another cross-sectional image group 36b in a second image capturing process, and another cross-sectional image group 36c in a third image capturing process (see FIG. 2). The cross sectional image groups 36a through 36c are stored temporarily in the memory 32. The time-series cross-sectional image group 36 is not limited to three cross-sectional image groups, and the number of groups is insignificant.

Figure 5A:
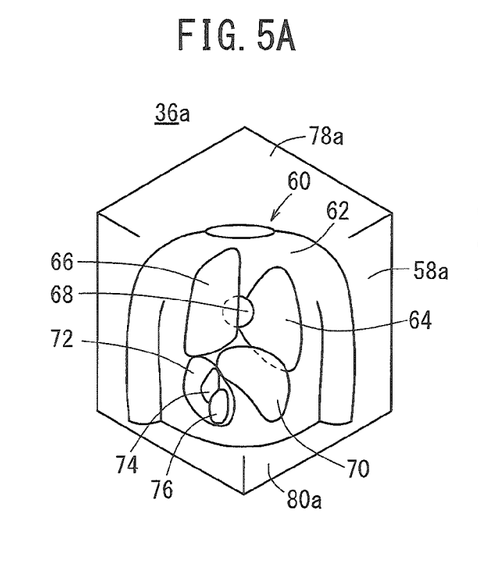
FIGS. 5A through 5C are schematic views showing a positional relationship between a human body image and image areas that are represented by respective cross-sectional image groups.
Figure 5B:
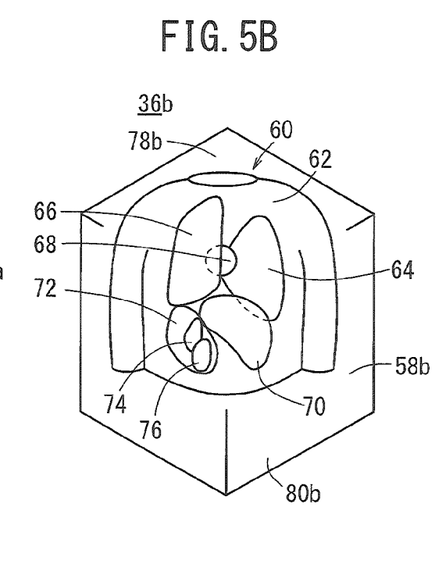
Figure 5C:
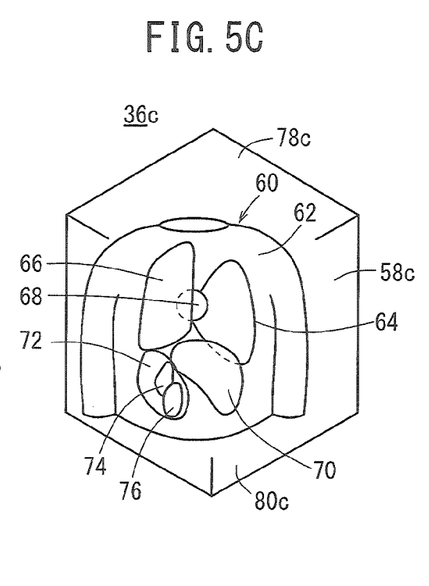

FIGS. 5A through 5C are schematic views showing a positional relationship between a human body image 60 and image areas 58a through 58c represented by the respective cross-sectional image groups 36a through 36c.

As shown in FIG. 5A, the cross-sectional image group 36a makes up a three-dimensional image area 58a. The image area 58a includes a human body image 60 of the subject 12 (see FIG. 1), which is captured from behind the subject 12. The human body image 60 includes a body region (hereinafter referred to simply as a "body 62"). The body 62 also includes a right lung 64, a left lung 66, a heart 68, a liver 70, a stomach 72, a spleen 74, and a kidney 76 disposed inside of the body 62.

As shown in FIG. 5B, the cross-sectional image group 36b makes up a three-dimensional image area 58b. Similar to the case of FIG. 5A, the image area 58b includes a human body image 60 with a body 62 having similar internal structural details.

As shown in FIG. 5C, the cross-sectional image group 36c makes up a three-dimensional image area 58c. Similar to the case of FIG. 5A, the image area 58c includes a human body image 60 with a body 62 having similar internal structural details.

In a case where slice images of the subject 12 are captured along the body axis (the first through third image capturing processes) by the X-ray CT apparatus 24 (see FIG. 1), a cross-sectional image group 36a (36b, 36c) is obtained, which represents a time series of cross-sectional images from an upper surface 78a (78b, 78c) to a lower surface 80a (80b, 80c). For example, the image capturing start position (the position of the upper surface 78b) in the second image capturing process differs from the image capturing start positions (positions of the upper surfaces 78a, 78c) in the first and third image capturing processes. Consequently, the human body image 60 in the image area 58b is positioned relatively higher than the human body images 60 in the image areas 58a, 58c. The image processing conditions in the third image capturing process also differ from the image processing conditions in the first and second image capturing processes, in such a manner that the human body image 60 in the image area 58c is positioned relatively more to the left than the human body images 60 in the image areas 58a, 58b.

In step S2, the region recognizer 48 recognizes the regions of the body 62 that are represented by the respective cross-sectional image groups 36a through 36c acquired in step S1. Various known algorithms may be applied for recognizing regions of the body 62. For example, among a plurality of reference regions, the region recognizer 48 may tentatively determine regions of the body 62 that are represented by the respective cross-sectional image groups 36a through 36c, generate a cost map of costs established depending on combinations of the cross-sectional image groups 36a through 36c and the reference regions, and correct the regions in order to minimize the cost of the cost map (for details, see Japanese Patent No. 4855141).

In step S3, the common region designator 50 designates a common region, which is commonly included in the cross-sectional image groups 36a through 36c. According to the first embodiment, the common region designator 50 designates, as a common region, a region that identifies a position along the Z-axis (see FIG. 4). The common region designator 50 may designate a common region according to an automatic instruction, based on the result of the image recognition process carried out in step S2, or according to an instruction entered by a doctor or a technician (hereinafter referred to as a "user") through a non-illustrated input means. The common region designator 50 may detect a slice number in the cross-sectional image group 36a, etc., from the Z-axis coordinate of the designated common region.

The common region may represent an upper or lower end of an organ having a relatively large size, which may be a lung, a liver, or the like, or may represent an organ having a relatively small size, which may be a certain bone, a navel, or the like. The common region may be a region that can be identified uniquely from the shape of the organ, e.g., a certain branch of a bronchus, an upper edge of an aortic arc, a starting point or branch of a left or right coronary artery, a branch of a pulmonary artery or a vein, or a certain branch of a liver artery, a portal vein, or a vein.

Figure 6A:
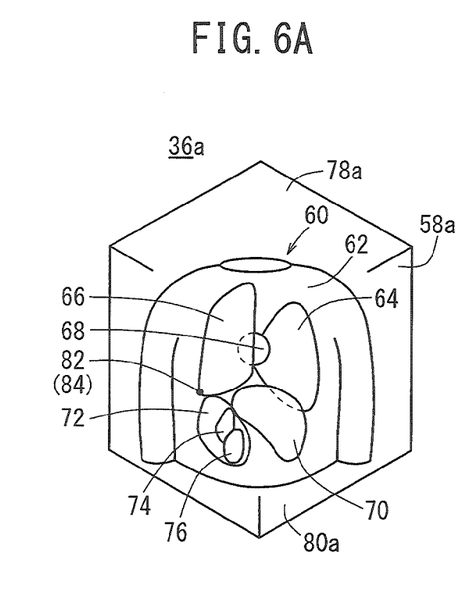
FIGS. 6A through 6C are schematic views illustrating a positioning process for the cross-sectional image groups.

As shown in FIG. 6A, it is assumed that the common region designator 50 has designated, as a common region 82, the lower end (marked with a solid dot) of the left lung 66, which is commonly included in the image areas 58a through 58c. Among the image groups in the time-series cross-sectional image group 36, one cross-sectional image group 36a is used as a positioning reference image (group), whereas the other cross-sectional image groups 36b, 36c are used as target images (groups). Reference numeral 84 represents a relative position of the common region 82 in the image area 58a, which will hereinafter be referred to as a "target position 84".

In step S4, the positioning processor 52 positions the common region 82 along the Z-axis (axial direction) with respect to the time-series cross-sectional image group 36. More specifically, the positioning processor 52 moves the image area 58b or the human body image 60 relatively based on the relationship between the target position 84 and the position (relative position) of the common region 82 in the image area 58b.

Figure 6B:
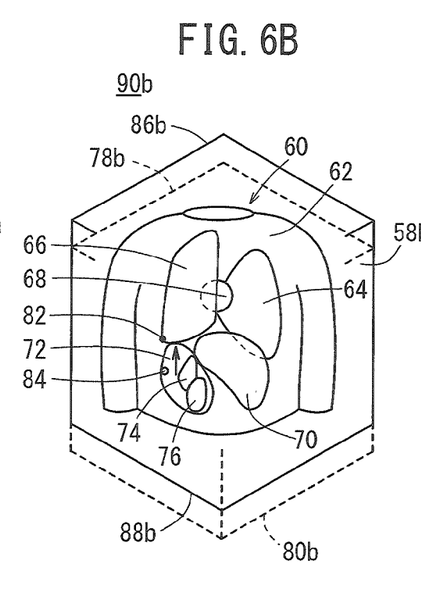

As shown in FIG. 6B, the relative position (marked with a solid dot) of the common region 82 is located slightly higher than the target position 84 (marked with an outlined dot). The positioning processor 52 translates the image area 58b (or the human body image 60) upwardly (or downwardly) by a predetermined distance, thereby bringing the common region 82 into positional alignment with the target position 84. At this time, a new cross-sectional image group (hereinafter referred to as an "adjusted image 90b") is obtained, which represents a time series of cross-sectional images from an upper surface 86b to a lower surface 88b.

In step S5, the positioning processor 52 positions the common region 82 along an X-Y plane (cross-sectional direction) normal to the Z-axis (axial direction), with respect to the time-series cross-sectional image group 36. More specifically, the positioning processor 52 moves the image area 58c or the human body image 60 relatively, based on the relationship between the target position 84 and the position (relative position) of the common region 82 in the image area 58c.

Figure 6C:
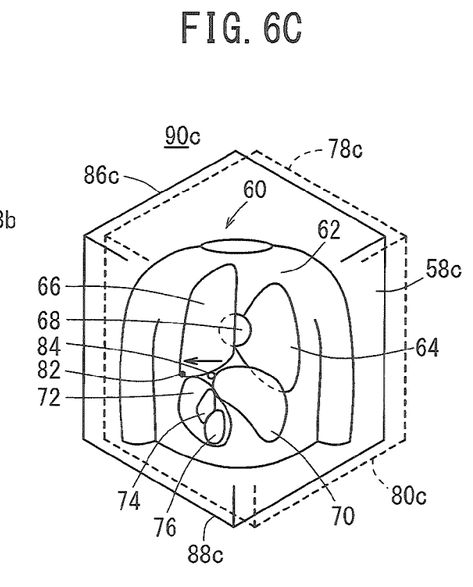

As shown in FIG. 6C, the relative position (marked with a solid dot) of the common region 82 is located slightly more to the left than the target position 84 (marked with an outlined dot). The positioning processor 52 translates the image area 58c (or the human body image 60) leftward (or rightward) by a given distance, thereby bringing the common region 82 into positional alignment with the target position 84. At this time, a new cross-sectional image group (hereinafter referred to as an "adjusted image 90c") is obtained, which represents a time series of cross-sectional images from an upper surface 86c to a lower surface 88c.

Even in case images of the same region in the same subject 12 are captured, the shape and position of the region may become changed depending on the times at which the images are captured. More specifically, the shape and position of the region may be altered because the shape of the body of the subject 12 may be changed, and various environmental conditions, including body movements during times that the images are captured, may be changed. To cope with this problem, the positioning processor 52 may perform a registration process on voxel data.

In step S6, the image compression processor 54 performs a moving-image compression process on the time-series images, and more specifically, the cross-sectional image group 36a as a positioning reference, and the adjusted images 90b, 90c that have been adjusted in steps S4 and S5. The moving-image compression process may comprise any of various known digital moving-image compression processes including MPEG-2, MPEG-4 (Motion Picture Expanding Group), and may be a lossless compression process or a lossy compression process. In view of compression efficiency and processing time, any of various processes may be selected in relation to interframe prediction, motion compensation, transform coding, etc.

As shown in FIGS. 6A through 6C, the cross-sectional image group 36a, the adjusted images 90b, 90c, and the human body image 60 are generated three-dimensionally in substantially the same position. Image changes between such images are either zero or minimal. In other words, in case the cross-sectional image group 36a and the adjusted images 90b, 90c are arrayed in a time series of slices, and thereafter, the cross-sectional image group 36a and the adjusted images 90b, 90c are compressed, it is possible to obtain compressed data 42 having an extremely high compression ratio. This aspect of the present invention is highly effective, especially in case the structure of the imaged subject 12 is known, or in case the time-dependent change of the imaged subject 12 is comparatively small.

In step S7, the image processing apparatus 26 stores the compressed data 42 that was obtained in step S6 in the memory 32 or in an external device (storage device 28). At this time, the image processing apparatus 26 also stores the positioning data 40 that was generated in step S5, the positioning data being associated with the compressed data 42. The image diagnosing apparatus 18 receives the compressed data 42 and the positioned data 40, and thereafter, the image diagnosing apparatus 18 performs a predetermined expanding process and a positioning process (inverted transform) on the compressed data 42 and the positioned data 40 in order to recover the time-series cross-sectional image group 36.

[Second Embodiment]

A second embodiment for saving and managing a cross-sectional image group generated by capturing slice images will be described below with reference to FIGS. 7 through 9.

Figure 7:
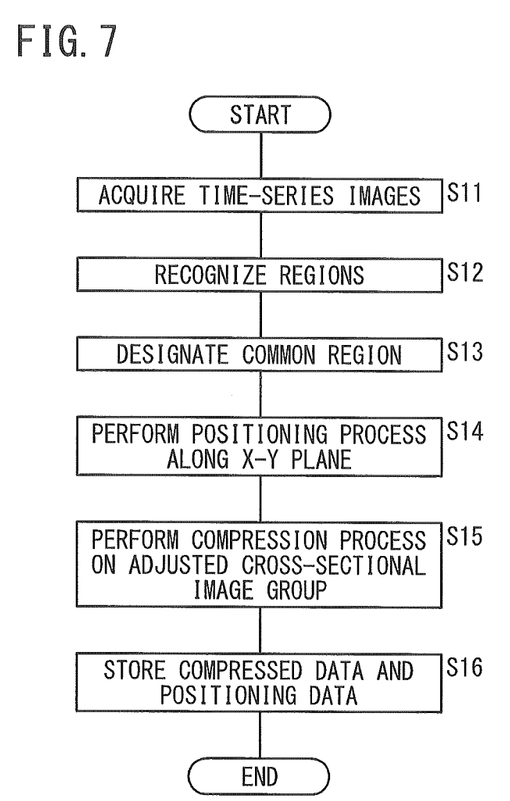
FIG. 7 is a second flowchart of the operation sequence of the image processing apparatus shown in FIGS. 1 and 2.

In step S11 of FIG. 7, the time-series image acquirer 46 acquires a cross-sectional image group 36a (see FIGS. 4 and 7) as time-series images 44. In step S12, the region recognizer 48 recognizes regions of a body, which are represented by the cross-sectional image group 36a that was acquired in step S11. Steps S11 and S12 are identical to steps S1 and S2 according to the first embodiment, and these steps will not be described in detail.

In step S13, the common region designator 50 designates at least one common region, which is commonly included in the raw images Io(1) through Io(15) of the cross-sectional image group 36a. According to the second embodiment, the common region designator 50 designates a region (structure) on which a positioning process is to be performed across a plurality of cross-sectional images. The common region designator 50 may designate, as a common region, at least one of a lung, a liver, a heart, a spleen, a kidney, a head, and a body. According to the second embodiment, it is assumed that the common region designator 50 designates a lung and a body.

In step S14, the positioning processor 52 positions the common region along an X-Y plane (cross-sectional direction) with respect to the cross-sectional image group 36a. More specifically, the positioning processor 52 positions the cross-sectional shape of the common region according to a rigid or a non-rigid registration process.

Figure 8:
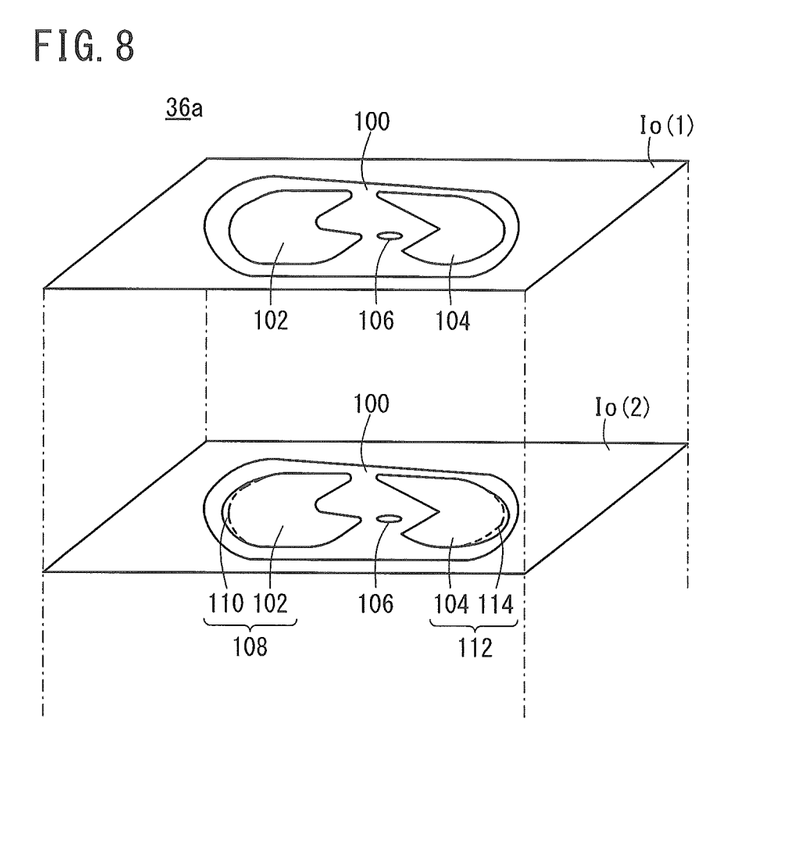
FIG. 8 is an enlarged partial view of the cross-sectional image group shown in FIG. 4.

As shown in FIG. 8, the raw image Io(1) of the cross-sectional image group 36a represents a body region (hereinafter referred to simply as a "body 100") of the subject 12 (see FIG. 1). The body 100, which has a generally elliptical shape, includes a right lung region (hereinafter referred to simply as a "lung 102"), a left lung region (hereinafter referred to simply as a "lung 104"), and an esophagus region (hereinafter referred to simply as an "esophagus 106"). For illustrative purposes, only image backgrounds and region profiles are shown in FIGS. 8 and 9.

The body 100 that is represented by the raw image Io(2) includes a right lung 108, which differs in shape from the right lung 102. More specifically, the right lung 108 bulges outwardly (to the left in FIG. 8) compared to the right lung 102. The differential region, which remains in a case where the right lung 102 is removed from the right lung 108, is referred to as a bulging region 110. The body 100 also includes a left lung 112, which differs in shape from the left lung 104. The left lung 112 bulges (to the right of FIG. 8) compared to the left lung 104. The differential region, which remains in a case where the left lung 104 is removed from the left lung 112, is referred to as a bulging region 114.

The positioning processor 52 brings the common region that is represented by the raw image Io(2) into positional alignment with the common region that is represented by the raw image Io(1), which is adjacent to the raw image Io(2) in the times series. According to a non-rigid registration process, for example, the positioning processor 52 deforms the right lung 108 of the raw image Io(2) into a right lung 108*r*, and deforms the left lung 112 of the raw image Io(2) into a left lung 112*r*.

Similar to the lungs, the body 100 also serves as a target to be positioned. However, the body 100 is of the same shape and remains in the same position in both of the raw images Io(1) and Io(2). Therefore, in spite of the positioning process, the body 100 remains unchanged in shape.

The positioning processor 52 brings the common region that is represented by a raw image Io(n+1) (where n is an integer of 2 or greater), into positional alignment with the common region that is represented by a raw image Io(n) that is adjacent to the raw image Io(n+1) in the times series. Consequently, a new cross-sectional image group 120*a* is obtained, which represents a time series of cross-sectional images {Io(1), Ir(2; 1) through Ir(N; N−1)}. The adjusted image Ir(2; 1) represents a cross-sectional image generated by bringing the common region that is represented by the raw image Io(2) into positional alignment with the common region that is represented by the raw image Io(1).

Figure 9:
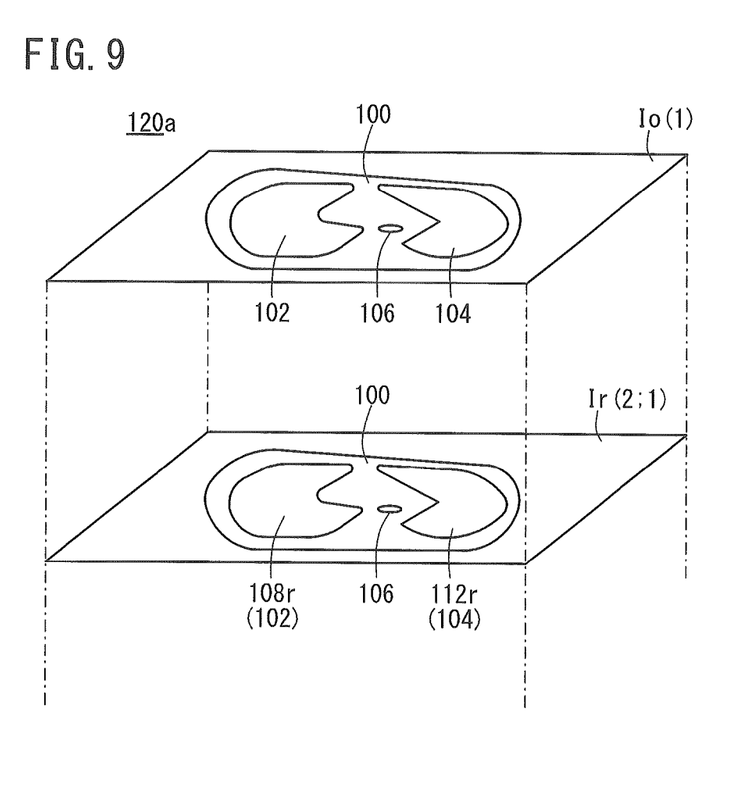
FIG. 9 is an enlarged partial view of a new cross-sectional image group, which is generated after the positioning process has been performed on the cross-sectional image group shown in FIG. 8.

As shown in FIG. 9, the regions, which are represented by the raw image Io(1) and the adjusted image Ir(2; 1), are generated two-dimensionally in substantially the same position. Image changes between these images are either zero or minimal. In other words, in case the raw image Io(1) and the adjusted image Ir(2; 1) are arrayed in a time series of slices, and thereafter, the raw image Io(1) and the adjusted image Ir(2; 1) are compressed, it is possible to obtain compressed data 42 having an extremely high compression ratio.

As described above, the image processing apparatus 26 includes the time-series image acquirer 46 that acquires time-series images 44 (the time-series cross-sectional image group 36, the time-series cross-sectional images 38) that are generated in a time series, the common region designator 50 that designates at least one common region 82 (102, 104) that is commonly included in the acquired time-series images 44, the positioning processor 52 that adjusts the time-series images 44 by bringing the common region 82 (108, 112) that is represented by at least one raw image of the time-series images 44 into positional alignment with the common region 82 (102, 104) that is represented by another raw image, and the image compression processor 54 that performs a moving-image compression process on new time-series images (the adjusted images 90*b*, 90*c*, and the new cross-sectional image group 120*a*) which have been adjusted.

Since the common region 82 (108, 112), which is represented by at least one raw image of the time-series images 44, is brought into positional alignment with the common region 82 (102, 104), which is represented by another raw image, at least within the common region 82 (102, 104), it is possible to generate time-series images having a small interframe image change. Thus, in a case where the adjusted new time-series images are compressed, the time-series images can be compressed with increased efficiency.

The present invention is not limited to the above embodiments, and various changes made be made freely to the embodiments without departing from the essence and scope of the invention. For example, the processing sequences according to the first and second embodiments may be combined with each other appropriately. In the above embodiments, specific examples of the compression process on medical images are illustrated. However, the present invention may also be applied to other fields apart from medical applications.

The invention claimed is:

1. An image processing apparatus comprising:
a time-series image acquirer configured to acquire time-series images comprising a plurality of raw images generated in a time series;
a common region designator configured to designate at least one common region that is commonly included in the time-series images acquired by the time-series image acquirer;
a positioning processor configured to adjust the time-series images by bringing a common region that is represented by at least one raw image of the time-series images into positional alignment with a common region that is represented by another raw image; and
an image compression processor configured to perform a moving-image compression process on the new time-series images adjusted by the positioning processor, wherein the positioning processor further acquires positioning data for positioning the common region,
the image processing apparatus further comprising a memory configured to store compressed data generated by the image compression processor, the compressed data being associated with the positioning data, and
wherein the time-series image acquirer acquires, as the time-series images, a cross-sectional image group generated by capturing slice images along an axial direction, and wherein the positioning processor adjusts the time-series images by positioning the common region along a cross-sectional direction normal to the axial direction.

2. The image processing apparatus according to claim 1, wherein the time-series image acquirer acquires, as the time-series images, a time series of cross-sectional image groups generated by capturing slice images along an axial direction, and
wherein the positioning processor adjusts the time-series images by positioning the common region along the axial direction.

3. The image processing apparatus according to claim 2, wherein the positioning processor adjusts the time-series images by using a position of the common region, which is represented by one raw image of the time-series images as a reference, and brings the common regions that are represented by remaining raw images into positional alignment with the reference.

4. The image processing apparatus according to claim 2, wherein the positioning processor adjusts the time-series images by positioning the common region along a cross-sectional direction normal to the axial direction.

5. The image processing apparatus according to claim 1, wherein the positioning processor adjusts the time-series image by bringing the common region, which is represented by each of the raw images, into positional alignment with the common region that is represented by an adjacent raw image in a time series.

6. The image processing apparatus according to claim 1, wherein the common region designator designates, as the common region, at least one of a lung, a liver, a heart, a spleen, a kidney, a head, and a body.

7. An image processing method comprising:
acquiring time-series images comprising a plurality of raw images generated in a time series;
designating at least one common region that is commonly included in the acquired time-series images;
positioning by adjusting the time-series images by bringing a common region that is represented by at least one raw image of the time-series images into positional alignment with a common region that is represented by another raw image; and
performing a moving-image compression process on the adjusted new time-series images,
wherein the positioning further acquires positioning data for positioning the common region,
the image processing method further comprising storing compressed data generated by the performing a moving-image compression process, the compressed data being associated with the positioning data, and
wherein the time-series image acquiring, as the time-series images, a cross-sectional image group generated by capturing slice images along an axial direction, and
wherein the positioning adjust the time-sereis images by positioning the common region along a cross-sectional direction normal to the axial direction.

8. A non-transitory computer-readable recording medium storing a program therein, the program causing a computer to carry out the steps of;
acquiring time-series images comprising plurality of raw images generated in a time series;
designating at least one common region that is commonly included in the acquired time-series images;
positioning by adjusting the time-series images by bringing a common region that is represented by at least one raw image of the time-series images into positional alignment with a common region that is represented by another raw image; and
performing a moving-image compression process on the adjusted new time-series images,
wherein the positioning further acquires positioning data for positioning the common region,
the non-transitory computer-readable recording medium further comprising storing compressed data generated by the performing a moving-image compression process, the compressed data being associated with the positioning data, and
wherein the time-series image acquiring, as the time-series images, a cross-sectional image group generated by capturing slice images along an axial direction, and
wherein the positioning adjusts the time-series images by positioning the common region along a cross-sectional direction normal to the axial direction.

9. The image processing apparatus according to claim 1, wherein the raw images generated in a time series are offset from each other.

10. The image processing apparatus according to claim 9, wherein the positioning processor shifts the designated at least one common region of each of the offset raw images to be in positional alignment aligned with each other.

11. The image processing apparatus according to claim 1, wherein the new time-series images are each in positional alignment with each other based on the at least one common region.

12. The image processing apparatus according to claim 1, wherein the common region designator designates the at least one common region in each of the plurality of raw images such that the positioning processor brings each of the plurality of raw images into positional alignment based on the designated at least one common region.

13. The image processing apparatus according to claim 1, wherein the positioning processor acquires the positioning data based on the designated at least one common region for each of the plurality of raw images.

14. The image processing apparatus according to claim 1, wherein the new time-series images are generated three-dimensionally in substantially a same position such that changes between each image of the new time-series images are substantially zero.

* * * * *